(12) United States Patent
Tung

(10) Patent No.: US 7,102,041 B2
(45) Date of Patent: Sep. 5, 2006

(54) CONTINUOUS PROCESS FOR PREPARING HALOGENATED COMPOUNDS

(75) Inventor: Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/007,036

(22) Filed: Dec. 8, 2004

(65) Prior Publication Data
US 2006/0122441 A1    Jun. 8, 2006

(51) Int. Cl.
C07C 21/18 (2006.01)
C07C 17/26 (2006.01)

(52) U.S. Cl. .............. 570/172; 570/101; 570/123; 570/170; 570/171

(58) Field of Classification Search ........ 570/101, 570/123, 170, 171, 172
See application file for complete search history.

(56) References Cited

U.S. PATENT DOCUMENTS 5,792,898 A   8/1998  Glover ............... 570/127
5,902,914 A   5/1999  Rygas et al.
5,917,098 A   6/1999  Bertocchio .......... 570/164
6,187,978 B1  2/2001  Rygas et al.
6,339,840 B1  1/2002  Kothari et al. ...... 717/149
6,399,839 B1  6/2002  Mathieu et al. ...... 570/172
6,441,256 B1  8/2002  Mathieu et al. ...... 570/172
6,500,993 B1  12/2002 Mathieu et al. ...... 570/127

FOREIGN PATENT DOCUMENTS

WO    WO 97/05090    * 7/1996

OTHER PUBLICATIONS

Burton et. al., J. Org. Chem. vol. 36, No. 18, 1971, p. 2596.*

* cited by examiner

Primary Examiner—Sikarl A. Witherspoon
Assistant Examiner—Chukwuma Nwaonicha
(74) Attorney, Agent, or Firm—Collen D. Szuch

(57) ABSTRACT

A process for preparing a haloalkane comprising: (a) contacting a haloalkane starting material with an alkene in the presence of an effective amount of a catalyst complex under conditions effective to facilitate an addition reaction and to form a product stream comprising a haloalkane product from the addition reaction, wherein the catalyst complex has a boiling point higher than that of the haloalkane product; and (b) recovering the haloalkane product from the product stream.

25 Claims, 1 Drawing Sheet

CONTINUOUS PROCESS FOR HCC-250 PRODUCTION

CONTINUOUS PROCESS FOR HCC-250 PRODUCTION

CONTINUOUS PROCESS FOR PREPARING HALOGENATED COMPOUNDS

FIELD OF THE INVENTION

The present invention relates to a process for preparing halogenated alkanes. More specifically, the present invention relates to a continuous process for preparing halogenated compounds using an addition reaction.

DISCUSSION OF THE BACKGROUND ART

Manufacturing of halogenated compounds is traditionally accomplished by using a batch or semi-batch process due to use of solid catalyst in liquid phase. Batch or semi-batch processes are not economical, resulting in relatively high cost products.

Addition reactions for preparing useful haloalkanes, such as 1,1,1,3,3-pentachloropropane (HCC-240) and 1,1,1,3,3 pentachlorobutane (HCC-360), are known in the art. Typically, in this reaction, a halogenated compound, such as, carbon tetrachloride, is added to an olefinic compound, such as, vinyl chloride, in the presence of a catalyst and under conditions sufficient to form a haloalkane product having a backbone longer than that of the haloalkane reactant. The halogenated product then is recovered by separating it from the reactants, catalyst and by-products using conventional techniques such as distillation. The conventional process is disclosed in U.S. Pat. No. 5,902,914, which is incorporated herein in its entirety.

A continuous process is also disclosed in U.S. Pat. No. 6,187,978, incorporated herein in its entirety, that can be used to manufacturing the HCC-240, HCC-360, etc. halogenated alkanes in a commercial scale process economically.

Both of the above prior arts dealt with making halogenated alkanes of a longer carbon chain by reacting a "halogenated" alkene with a halogenated alkane.

The present invention discloses a continuous process that can be used in a commercial operation for the manufacturing of halogenated alkane with increasing carbon chain by reacting a "non-halogenated" alkene, such as ethylene, propylene, butene, etc. with a halogenated alkane. This continuous process can also reduce manufacturing cost for production of halogenated compounds.

The present inventor has uniquely discovered that alkenes can be used in the manufacturing of halogenated alkanes in place of halogenated alkenes even though they must be used at a higher pressure, are more flammable and may be explosive. The present inventor has discovered that it is desirable to use alkenes versus halogenated alkenes because alkenes are less expensive and react faster, thus making them more commercially desirable. Moreover, alkenes produce products that are at least one halogen less than those produced from equivalent halogenated alkenes.

SUMMARY OF THE INVENTION

A continuous process for the production of haloalkane comprising: (a) contacting a haloalkane starting material with an alkene starting material in the presence of an effective amount of a catalyst complex under conditions effective to facilitate an addition reaction and to form a product stream containing a haloalkane product from the addition reaction, wherein the catalyst complex has a boiling point higher than that of the haloalkane product; and (b) recovering the haloalkane product from the product stream.

The boiling point of the catalyst complex exceeds the boiling point of the haloalkane product by no less than about 20° C. The catalyst complex preferably has a solid substrate. Preferably, the catalyst complex is thermally stable up to about 90° C. The catalyst complex comprises a metallic catalyst and an organic ligand.

The metallic catalyst is an elemental powder, salt, or organometallic compound of a transition metal. The catalyst complex is selected from the group consisting of a copper-containing catalyst/a primary amine; an iron-containing catalyst/an amide; an iron-containing catalyst/a phosphate and; a copper-containing catalyst/nitrile.

The copper-containing catalyst is selected from the group consisting of cuprous chloride, cuprous bromide, cuprous cyanide, cuprous sulfate, and cuprous phenyl.

The organic ligand is at least one selected from the group consisting of: amines, nitrites, amides, phosphates and phosphites. The organic ligand is at least one amine selected from the group consisting of: stearylamines, laurylamines, cyclohexylamines, octylamines, 2-ethyl-1-hexylamines, 2-octylamines, tertoctylamines, diaminododecane ($C_{12}H_{28}N_2$), hexamethylenediamine, and tetramethylenediamine The iron-containing catalyst is selected from the group consisting of: iron powder, cuprous chloride, iron ball, ferric chloride, and ferrous chloride, and the organic ligand is selected from the group consisting of amines, nitrites, amides, phosphates and phosphites. The iron-containing catalyst is ferrous chloride and the organic ligand is tributylphosphate. Alternatively, the iron-containing catalyst is ferrous chloride and the organic ligand is triphenylphospate.

The haloalkane starting material is at least one selected from the group consisting of: carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane.

The alkene according to the present invention has the general formula:

$$C_qH_r$$

wherein q is an integer in the range between about 2 to 200 and r is an integer in the range between about 0 to 2q. The alkene is at least one alkene selected from the group consisting of: ethylene, propylene, butene and hexene.

The mole ratio of the haloalkane to the alkene is in the range between about 1.2:1 to 10:1.

The product stream comprises a portion of the catalyst complex; and step (b) comprises separating the catalyst complex from the haloalkane product through distillation; and the process further comprises: (c) recycling the catalyst complex.

It is preferably that the catalyst complex is separated from the haloalkane product by flash distillation (FIG. 1).

It is also desirable that step (b) further comprises the step of introducing a chelating agent.

The product stream also comprises the catalyst complex, wherein the haloalkane product is separated from the product stream by distilling the product stream into a top stream comprising the haloalkane product and a bottom stream comprising the catalyst complex.

The process further comprising distilling the top stream into a second top stream, which is recycled, and a second bottom stream comprising the haloalkane product.

The process further comprises distilling the product stream into a top stream comprising volatile reactants which are recycled, and a bottom stream comprising the catalyst complex and the haloalkane product; and further distilling the bottom stream into a second top stream comprising the haloalkane product and a second bottom stream comprising the catalyst complex which is recycled.

DETAILED DESCRIPTION OF THE PREFERRED EMBODIMENT

Figure 1:
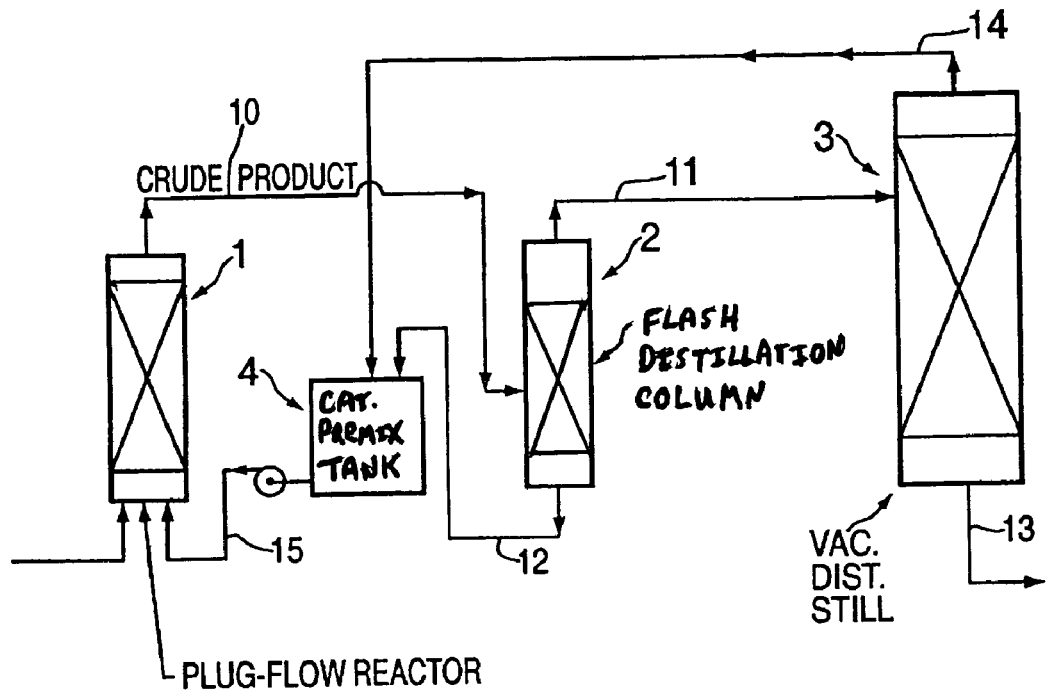
FIG. 1 is a schematic diagram of continuous process for HCC-250 according to the present invention using a flash distillation for separating catalyst complex from the crude product.

The present invention provides a continuous, high-capacity process for the production of halogenated alkanes using a catalyst complex having a higher boiling point than that of the reaction product. Since its boiling point is higher, the catalyst complex is readily separated from the haloalkane product through distillation and may be recycled along with unused reactants. Furthermore, if its boiling point is sufficiently high or if it is immobilized on a nonvolatile substrate, the catalyst complex tends not to be vaporized during the reaction and remains in the reactor. With either approach, the haloalkane product is conveniently separated from the catalyst complex, thus minimizing disruptions to the process and promoting a continuous production.

The present invention is directed to a continuous process for the production of haloalkane from the reaction of haloalkane and an alkene. For examples, the production of 1,1,1,3-tetrachloropropane (HCC-250fb) is generated via the below equation:

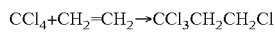

The catalysts which may be used in this reaction include iron powder and iron chlorides or halides, e.g., cuprous chloride, cupric chloride, or other metal chlorides or halides.

In order to make the process continuous, the catalyst complex has to have a higher boiling point that that of the haloalkane product. The co-catalyst that forms the catalyst complex is very important. Co-catalysts should have relatively high boiling points. Examples of such co-catalysts include phosphate having a backbone of three (3) or more carbons, nitrites having a backbone of three (3) or more carbons, amides having a backbone of two (2) or more carbons; primary amines selected from the group consisting of: stearylamines, laurylamines, octylamines, 2-ethylhexylamine, 2-octylamine, 2-ethylhexylamine, 2-octylamine, tert-octylamine, diaminedodecane ($C_{12}H_{28}N_2$), and combinations thereof.

The heavy catalyst complex allows the process to continuously take off haloalkane product from the reaction and catalyst complex can be continuously recycled back to the reactor.

One aspect of the present invention is characterized by an addition reaction in which halogenated compounds are prepared using an effective amount of a catalyst complex having a boiling point above that of the halogenated compound. In a preferred embodiment, the process comprises: (a) contacting a haloalkane starting material with non-halogenated alkene starting material in the presence of an effective amount of the catalyst complex under conditions effective to facilitate an addition reaction and to form a product stream comprising a haloalkane product from the addition reaction; and (b) recovering the haloalkane product from the product stream.

An important consideration in the process of the present invention is the catalyst complex which should have several properties/attributes. First, the catalyst complex must promote an addition reaction between the haloalkane and alkene starting materials. To this end, the catalyst complex should form either a homogeneous system in which the catalyst is miscible in the starting materials, or a heterogeneous solution in which just a portion of the catalyst complex is miscible in the starting material. The immiscible portion in the heterogeneous solution may be, for examples, a solid substrate to which a catalytic organic ligand is anchored. Alternatively, the immiscible portion in a heterogeneous solution may be fine particles of catalyst.

Second, the catalyst complex must have a boiling point above that of the haloalkane product of the addition reaction. A significant difference in the boiling points is preferred to facilitate separation of the catalyst complex from the haloalkane product—the greater the difference, the more readily the two components can be separated. Preferably, the boiling point of the catalyst complex exceeds the boiling point of the haloalkane product by no less than about 10° C., and more preferably by not less than about 20° C. Furthermore, it may be preferable to immobilize the catalyst complex on a non-volatile substrate to minimize the vaporization of the catalyst complex so that little or no catalyst complex is present in the product stream, and no post-reaction separation of the catalyst complex and the haloalkane product is required.

Third, the catalyst complex should be thermally stable, meaning that it does not thermally degrade during the addition reaction or in the post-reaction recovery stages. Preferably, the catalyst complex is stable up to about 90° C., and more preferably up to about 100° C.

It has been found that metallic catalysts and organic ligands form suitable catalyst complexes. As used herein, the term "metallic catalyst" refers to elemental powders, salts, and organometallic compounds of the transition metals. The preferred metallic catalysts include copper and iron. Exemplary cuprous salts and organometallic cuprous cyanide, cuprous sulfate, and cuprous phenyl. Exemplary iron salts and organometallic ferrous compounds include, without limitation, ferrous chloride, ferric chloride, tris(2,2'-bipyridine) iron (II) hexafluorophosphate. Exemplary copper and iron powders preferably are fine, substantially pure powders having a particle size no greater than about 100 mesh, and preferably no greater than about 325 mesh. The more preferred metallic catalysts include cuprous chloride and iron powder.

The organic ligand should be capable of forming a complex with a metallic catalyst having the properties and attributes as described above. Suitable organic ligands include, amines, nitrites, amides, phosphates and phosphites.

More specifically, it has been found that primary and secondary amines having a backbone of four or more carbons tend to form a catalyst complex having the above-mentioned attributes. Examples of preferred amines include, for example, stearylamines, laurylamines, cyclohexylamines, octylamines, 2-ethyl-1-hexylamines, 2-octylamines, tertoctylamines, diaminododecane ($C_{12}H_{28}N_2$), hexamethylenediamine, and tetramethylenediamine. More preferred amines include, for example, cyclohexylamine, octylamine and tetramethylenediamine.

It has been found by the present inventor that nitrile groups having a backbone of three or more carbons tend to form catalyst complexes having the above-mentioned attributes. Examples of preferred nitrites include, for example, acetonitrile, pentanenitrile, benzonitrile, and tolunitriles. More preferred nitrites include, for example, acetonitrile and pentanenitrile.

It has also been found that amides having a backbone of two or more carbons tend to form catalyst complexes having the above-mentioned attributes. Examples of preferred amides, form example, N-ethylacetamide, acetanilide, aceto-p-toluidide, and hexamethylenephosphomamide. More preferred amides include, for example, hexamethylenephosphoramide.

Phosphates having a backbone of three or more tend to form catalyst complexes having the above-mentioned attributes. Examples of preferred phosphates include, for example, trimethylphosphate, triethylphosphate, tributylphospate, and triphenylphosphate. More preferred phosphates include, for example, tributylphospate.

The choice of which specific organic ligand to use tends to depend on the catalyst used. Generally, although not limited by this theory, it has been found that amines and nitrites are particularly effective in forming suitable catalyst complexes with copper-containing catalysts; amides and phosphates are particularly effective in forming suitable catalyst complexes with iron-containing catalysts.

Particularly preferred combinations of catalysts and organic ligands are provided below in Table 1.

TABLE 1

Preferred Complexes

| Combination | Catalyst | Organic Ligand |
|---|---|---|
| 1 | Cuprous chloride | Stearylamine |
| 2 | Cuprous chloride | Laurylamine |
| 3 | Cuprous chloride | Cyclohexylamine |
| 4 | Cuprous chloride | Octylamine |
| 5 | Cuprous chloride | 2-ethylhexylamine |
| 6 | Cuprous chloride | 2-octylamine |
| 7 | Cuprous chloride | Tert-octylamine |
| 8 | Cuprous chloride | Diaminododecane $C_{12}H_{28}N_2$ |
| 9 | Iron powder | Tribuylphosphate |
| 10 | Iron powder | Hexamethylenephosphoramide |
| 11 | Iron powder | Triphenylphosphate |
| 12 | Ferric chloride | Tributylphosphate |
| 13 | Ferrous chloride | Tribuylphosphate |
| 14 | Ferrous chloride | Triphenylphospate |

The specific combination of catalyst and organic ligand used tends to depend upon their commercial availability, the reactants used, and the desired haloalkane product. Mixtures of the above combination (i.e., mixture of 12 and 13) can also work very well. For example, it has been found that, in the production of 1,3,3,3-tetrachloropropane (HCC-250) from ethylene and carbon tetrachloride, the preferred catalyst complex is cuprous chloride-cyclohexyl amine, commercially available from Aldrich, Milwaukee, Wis., USA.

As mentioned above, the catalyst complex of the present invention also may include a solid/non-volatile substrate on which an organic ligand is immobilized. In other words, a solid/non-volatile substrate may be functionalized with an organic ligand such that the catalyst forms a miscible complex with the organic ligand functionality while the substrate remains immiscible. Since the catalyst complex is immobilized on a non-volatile substrate it tends not to vaporize during the reaction, and, consequently, there is no need to separate the haloalkane product from the catalyst complex in post-reaction processing. Preferably, the substrate is an ion exchange resin having organic ligand functionality. Many such ion exchange resins are known. One example is Amberline resin which contains amine functionality and is commercially available through Rohm & Haas, Philadelphia, Pa., USA.

Generally, the mole ratio of catalyst to organic ligand ranges from about 0.01:1 to about 50:1, and preferably from about 0.1:1 to about 3:1. For example, the mole ratio of cuprous chloride to cyclohexylamine is about 0.05:1 to about 2.0:1, preferably about 0.02:1 to 1.0:1, and, more preferably, about 0.1:1 to about 0.7:1. The mole ratio of iron powder to tributylphosphate may be about 0.05:1 to about 10.0:1, preferably about 1.0:1 to about 3.0:1, and more preferably between about 1.5:1 to about 2.5:1.

The catalyst complex is used in an amount sufficient to catalyze the reaction of the haloalkane and alkene reactants. Preferably, the concentration of the catalyst in the reaction mixture ranges from about 0.01 to about 10 wt. %, preferably from about 1 to about 5 wt. %, and more preferably from about 1.5 to about 2.5 wt. %. For example, suitable results have been obtained using 1 wt. % of cuprous chloride cyclohexylamine to catalyze the reaction of carbon tetrachloride and ethylene to form HCC-250.

The reactants used in the process of the present invention comprise a haloalkane and a non-halogenated alkene. A suitable haloalkane reactant in the process of the present invention has the following formula:

$$C_nH_mX_p \qquad (1)$$

wherein n is an integer from about 1 to 200, preferably from about 1 to 20, and more preferably from about 1 to 4; each X is an independently selected halogen, preferably fluorine or chlorine, and more preferably chlorine; and m and p are integers selected from 0 to 2n+2; provided that m+p=2n+2.

Exemplary haloalkanes include, without limitation, carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane. Preferred haloalkanes include carbon tetrachloride, 1,1,1-trichloroethane, and 1,1,1-trichlorotrifluoroethane.

A suitable non-halogenated alkene in the process of the present invention has the following general formula:

$$C_qH_r \qquad (2)$$

wherein q is an integer range from about 2 to 200, preferably from about 2 to 20, and more preferably from about 2 to 4; and r is an integer from 0 to 2q; preferably r=2q.

Exemplary alkenes include, without limitation, ethylene, propylene, butene, hexene, etc.

The specific haloalkane and non-halogenated alkenes starting materials used depends in large part on their commercial availability and the desired haloalkane product. For example, to prepare HCC-250, the preferred reactants are carbon tetrachloride, available from Vulcan Chemicals of Birmingham, Ala., USA, and ethylene, available from ExxonMobil Chemical Company, Houston, Tex., USA.

The concentration of the haloalkane and alkene starting materials is determined by the desired haloalkane product and the stoichiometry of the addition reaction. Preferably, a stoichiometric excess of the haloalkane is used. The mole ratio of haloalkane to alkene is generally from about 1.2:1 to about 10:1, and preferably from about 1.5:1 to about 4:1.

The reactants are subjected to condition sufficient to effect an addition reaction to produce a haloalkane product having a carbon chain longer than that of the haloalkane reactant. The haloalkane product has the following general formula:

$$C_u H_v X_w \qquad (3)$$

wherein u is an integer greater than n which is an integer from about 1 to 200, preferably from about 1 to 20, and more preferably n+q; X is an independently selected halogen, preferably fluorine or chlorine, and more preferably chlorine; and v and w are integers from 0 to 2u+2; provided that v+w=2u+2, preferably $2 \leq w \leq 2u+2$, and more preferably $3 \leq w \leq 2u+2$.

Exemplary haloalkane products include, without limitation, HCC-250, HCC-370, etc.

To effect favorable selection and yields, it is preferable to achieve good mixing of at least a portion of the catalyst complex in the reactions. To this end, the catalyst may be added to the reactor containing the haloalkane, alkene and organic ligand, or the haloalkane and alkene may be added to a reactor containing the catalyst and organic ligand. Preferably, however, first the catalyst, organic ligand and haloalkane are mixed, then the mixture is degassed by quick partial evacuation of the vapors, and finally the alkene is added to the mixture.

The reaction should be conducted under operating conditions sufficient to effect the addition reaction of the haloalkane and the alkene in a continuous process. The specific reaction conditions are determined by the desired product, reactants and catalyst used. For example, in the preparation of HCC-250, suitable results have been obtained at temperatures from about 40° C. to about 180° C., and, preferably, from about 50° C. to about 110° C. Likewise, contact times tend to vary according to the catalyst used and the reaction conditions. For example, in the preparation of HCC-250, suitable results have been obtained with contact times from about 10 seconds to about 10 hours, and preferably from about 1 minute to about 5 hours. Furthermore, it has been found that agitation is helpful to increase contact between the reactants and the catalyst complex.

Reaction pressure typically is maintained by removing a product stream containing the haloalkane product from the reactor. Generally, the pressure should be maintained to achieve the desired contact times. It has been found that reaction pressures of about 1 psi to about 400 psi are preferred, while pressure of about 50 to about 200 psi are more preferred.

The reaction preferably is conducted continuously to produce a product stream containing halogenated product, plus volatile reactants and/or by-products. Depending on the catalyst system used, the product stream may also contain a portion of the catalyst complex. At this point, the product stream is subjected to conventional separation techniques and apparatus, such as distillation, to recover the halogenated compound. Traditionally, such recovery was complicated by the fact that the organic ligand tended to flash off during distillation leaving behind a solid catalyst in the distillation column. This would require interrupting the continuous process to remove the solid catalyst from the column.

The present invention, however, overcomes this problem by using a thermally-stable, high-boiling point catalyst complex as described above. The organic ligand in the catalyst complex of the present invention tends not to flash off and leave a solid residue behind. On the contrary, its high boiling point tends to facilitate recovery through distillation. Furthermore, in the case where a solid substrate is used, the catalyst complex is immobilized and thereby does not leave the reactor during the process. Thus, no separation is required.

In recovering the haloalkane product from the product stream, it is preferred to minimize the decomposition of the haloalkane product. That is, under high temperatures, the catalyst tends to react with the haloalkane product, thereby resulting in its decomposition. One approach to minimizing product decomposition is to minimize the contact time between the catalyst and the haloalkane product. In a preferred embodiment, this is accomplished by flashing off the haloalkane product along with the more volatile constituents of the product stream, leaving behind the less-volatile catalyst complex.

Alternatively or additionally, the haloalkane product may be "insulated" from the catalyst by chelating the catalyst with a chelating agent. Suitable chelating agents include, for example, organic phosphates, while tributylphosphate is preferred. Although the addition of a chelating agent is helpful in minimizing product decomposition, it nevertheless complicates the recovery of the haloalkane product by introducing another constituent to the process that eventually must be removed if the process is to be conducted continuously. Therefore, the use of a chelating agent may necessitate additional distillation steps.

The detrimental effect of introducing a chelating agent to the process can be obviated if the chelating agent is the same as the organic ligand used to form the catalyst complex. If the chelating agent is the same, there is no need to remove it, and, consequently, it can be recycled along with the catalyst complex back to the reactor.

Figure 2:
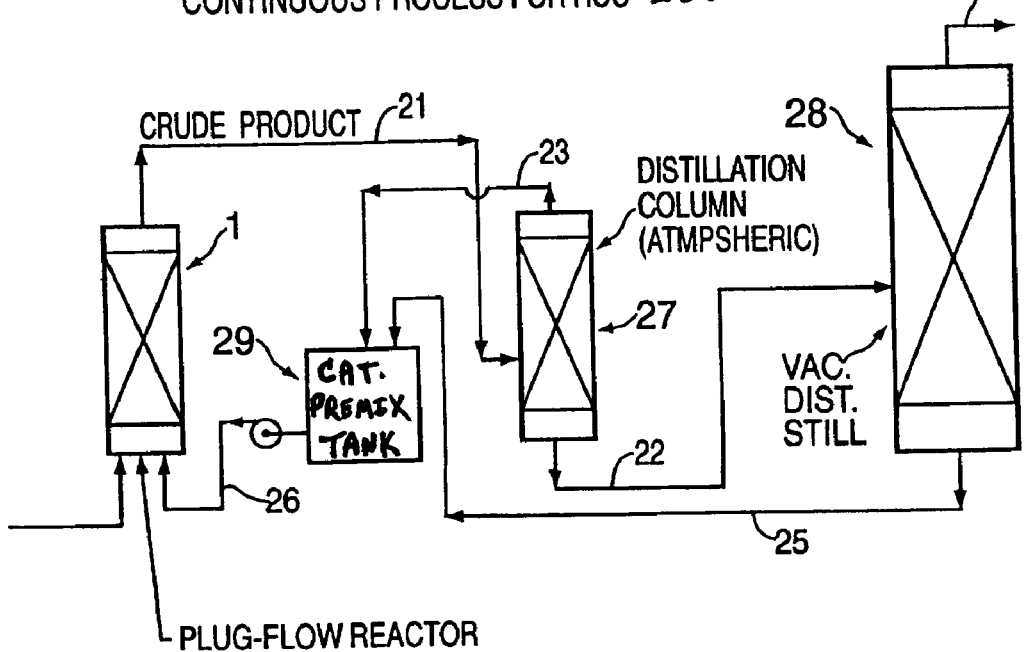
FIG. 2 is a schematic diagram of continuous process for HCC-250 also according to the present invention using a regular distillation column combined with a vacuum distillation column for the separation and recycle of catalyst complex.

Preferred embodiments of the systems for recovering the haloalkane product from the product stream are depicted, but not limited, schematically in FIGS. 1 and 2. In FIG. 1, the product stream 10 is continuously removed from a plug-flow reactor 1 (or a continuous stirred reactor). Product stream 10 is fed into a flash distillation column where it is split into a top stream 11 and a bottom stream 12. The top stream 11 contains the haloalkane product along with more volatile compounds, such as the reactants, and the bottom stream 12 contains the catalyst complex.

Top stream 11 is fed to a distillation column 3 where it is further separated into a second top stream 14 and a second bottom stream 13. The second bottom stream 13 contains a purified form of the haloalkane product. This particular recover scheme facilitates stripping the haloalkane product from the more volatile compounds.

The bottom stream 12 and the second top stream 14 optionally may be combined in catalyst pre-mix tank- and recycled to the reactor 1 in recycle stream 15.

FIG. 2 shows an alternative embodiment of recovering the haloalkane product from the product stream. As shown, a product stream 21 is removed from a plug flow reactor 1 (or continuous stirred reactor), and is fed into a distillation column 27. Distillation column 27 is operated at conditions that separate product stream 21 into a top stream 23 containing volatile reactants, and a bottom stream 22. Bottom stream 22 contains the halogenated product and catalyst complex and is fed into vacuum distillation column 28. Vacuum distillation column 28 separates bottom stream 22 into a second bottom stream 25 containing the catalyst complex and a second top stream 24 containing a relatively purified form of the halogenated product. As mentioned above, to minimize decomposition of the halogenated product, an additional chelating agent may be used to chelate the catalyst. Preferably, the chelating agent is the same as the organic ligand to avoid the need for additional distillation steps to remove the chelating agent from the process.

Top stream 23 and the second bottom stream 25 optionally may be combined in a catalyst pre-mix tank 29 and then recycled to the reactor 1 in recycle stream 26.

EXAMPLE 1

To a 0.5 inch by 40 inch plug flow reactor, a mixture (50/50 mole %) of ethylene and carbon tetrachloride is fed at about 1.5 g/min. A catalyst mixture of cuprous chloride, laurylamine and carbon tetrachloride, which is prepared in a catalyst pre-mix tank (2 liter), is also fed to the reactor simultaneously at about 2 g/min. The reactor is operated at 80–100° C. and controlled at about 30 psig. The effluent of the plug flow reactor is fed to a distillation column, which is operated at atmospheric pressure and about 80° C. The unreacted carbon tetrachloride with trace amounts of ethylene are distilled off from this distillation column and fed to the catalyst pre-mix tank. The bottom mixture from this distillation is fed to a second distillation that is operated under vacuum, at about 50 mmHg and 80–90° C. The crude HCC-250 product is collected from the top of the column. The bottom mixture that contains the catalyst mixture, cuprous chloride and laurylamine is fed back to the recycle column. The crude HCC-250 contains 1.4 grams of HCC-250. The yield is greater than 90%.

EXAMPLE 2

To a 1 liter glass-lined autoclave equipped with an agitator, a mixture (50/50 mole %) of ethylene and carbon tetrachloride is fed at about 1.5 g/min. A catalyst mixture of ferric chloride, tributyl phosphate and carbon tetrachloride, which is prepared in a catalyst pre-mix tank (2 liters), is also fed to the reactor simultaneously at about 2 g/min. The reactor is operated at about 100° C. and controlled at less than 80 psig. The product mixture is removed continuously by using a dip tube, which is inserted about ⅔ of the autoclave. The product mixture is fed to a distillation column, which is operated at atmospheric pressure and about 80° C. The unreacted carbon tetrachloride with trace amounts of ethylene are distilled off from this distillation column and fed to the catalyst pre-mix tank. The bottom mixture from this distillation is fed to a second distillation that is operated under vacuum, at about 50 mmHg and 80–90° C. The crude HCC-250 product is collected from the top of the column. The bottom mixture that contains the catalyst mixture, ferric chloride and tributyl phosphate is fed back to the catalyst pre-mix tank. The crude HCC-250 contains 1.35 grams of HCC-250. The yield is greater than 90%.

What is claimed is:

1. A continuous process for preparing a haloalkane comprising:
   (a) contacting a haloalkane starting material with a non-halogenated alkene in the presence of an effective amount of a metal catalyst complex comprising a metal and an organic ligand under conditions effective to facilitate an addition reaction and to form a product stream comprising a haloalkane product from said addition reaction, wherein said metal catalyst complex has a boiling point higher than that of said haloalkane product, the metal is a transition metal, and the organic ligand is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms; and
   (b) recovering said haloalkane product from said product stream.

2. The process of claim 1, wherein the boiling point of said catalyst complex exceeds the boiling point of said haloalkane product by no less than about 20° C.

3. The process of claim 1, wherein said catalyst complex has a solid substrate.

4. The process of claim 1, wherein said catalyst complex is thermally stable up to about 90° C.

5. The process of claim 1, wherein the metal of the metal catalyst complex consists of a metal selected from the group consisting of copper and iron.

6. The process of claim 1, wherein said metallic catalyst is an elemental powder, salt, or organometallic compound of a transition metal.

7. The process of claim 5, wherein said catalyst complex is selected from the group consisting of: a copper-containing catalyst's primary amine; an iron-containing catalyst/an amide; an iron-containing catalyst/a phosphate and; a copper-containing catalyst/nitrile.

8. The process of claim 7, wherein said copper-containing catalyst is selected from the group consisting of cuprous chloride, cuprous bromide, cuprous cyanide, cuprous sulfate, and cuprous phenyl.

9. The process of claim 5, wherein said metallic catalyst is an elemental powder, salt, or organometallic compound of copper or iron.

10. The process of claim 9, wherein said organic ligand is at least one amine selected from the group consisting of: stearylamines, laurylamines, cyclohexylamines, octylamines, 2-ethyl-1-hexylamines, 2-octylamines, tertoctylamines, diaminododecane ($C_{12}H_{28}N_2$), hexamethylenediamine, and tetramethylenediamine.

11. The process of claim 7, wherein said iron-containing catalyst is selected from the group consisting of: iron powder, iron ball, ferric chloride, and ferrous chloride, and said organic ligand is selected from the group consisting of amines, nitrites, amides, phosphates and phosphites.

12. The process of claim 11, wherein said iron-containing catalyst is ferrous chloride and said organic ligand is tributylphosphate.

13. The process of claim 11, wherein said iron-containing catalyst is ferrous chloride and said organic ligand is triphenylphospate.

14. The process of claim 1, wherein said haloalkane starting material has the general formula: haloalkane reactant in the process of the present invention has the following formula:

$$C_nH_mX_p$$

wherein n is an integer from about 1 to 200; each X is an independently selected halogen; and m and p are integers selected from 0 to 2n+2: provided that m+p=2n+2.

15. The process of claim 14, wherein said haloalkane starting material is at least one selected from the group consisting of: carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane.

16. The process of claim 1, wherein said alkene has the general formula:

$$C_qH_r$$

wherein q is an integer in the range between about 2 to 200 and r is an integer.

17. The process of claim 16, wherein said alkene is at least one alkene selected from the group consisting of: ethylene, propylene, butene and hexene.

18. The process of claim 1, wherein the mole ratio of said haloalkane to said alkene is in the range between about 1.2:1 to 10:1.

19. The process of claim 14, wherein said haloalkane product has the following general formula:

$$C_uH_vX_w$$

wherein u is an integer greater than n; X is an independently selected halogen; and v and w are integers from between about 0 to 2u+2; provided that v+w=2u+2.

20. The process of claim 1, wherein said product stream comprises a portion of said catalyst complex; and step (b) comprises separating said catalyst complex from said haloalkane product through distillation; and said process further comprises:

(c) recycling said catalyst complex.

21. The process of claim 20, wherein said catalyst complex is separated from said haloalkane product by flash distillation.

22. The process of claim 20, wherein said step (b) further comprises the step of introducing a chelating agent.

23. The process of claim 1, wherein said product stream also comprises said catalyst complex, wherein said haloalkane product is separated from said product stream by distilling the product stream into a top stream comprising said haloalkane product and a bottom stream comprising said catalyst complex.

24. The process of claim 23 further comprising distilling said top stream into a second top stream, which is recycled, and a second bottom stream comprising said haloalkane product.

25. The process of claim 1, further comprising distilling the product stream into a top stream comprising volatile reactants which are recycled, and a bottom stream comprising said catalyst complex and said haloalkane product; and further distilling said bottom stream into a second top stream comprising said haloalkane product and a second bottom stream comprising said catalyst complex which is recycled.

* * * * *

(12) EX PARTE REEXAMINATION CERTIFICATE (8264th)
United States Patent
Tung

(10) Number: US 7,102,041 C1
(45) Certificate Issued: May 24, 2011

(54) CONTINUOUS PROCESS FOR PREPARING HALOGENATED COMPOUNDS

(75) Inventor: Hsueh Sung Tung, Getzville, NY (US)

(73) Assignee: Honeywell International Inc., Morristown, NJ (US)

Reexamination Request:
No. 90/010,730, Nov. 9, 2009

Reexamination Certificate for:
Patent No.: 7,102,041
Issued: Sep. 5, 2006
Appl. No.: 11/007,036
Filed: Dec. 8, 2004

(51) Int. Cl.
*C07C 21/18* (2006.01)
*C07C 17/26* (2006.01)

(52) U.S. Cl. .................. 570/172; 570/101; 570/123; 570/170; 570/171

(58) Field of Classification Search .................. None
See application file for complete search history.

(56) References Cited

U.S. PATENT DOCUMENTS

| | | | |
|---|---|---|---|
| 3,862,978 A | 1/1975 | Decker et al. |
| 4,605,802 A | 8/1986 | Astrologes |
| 5,091,602 A | 2/1992 | Park et al. |
| 5,608,127 A | 3/1997 | Gumprecht |
| 5,786,400 A | 7/1998 | Brock et al. |
| 5,895,792 A | 4/1999 | Rotermund et al. |
| 6,300,532 B1 | 10/2001 | Van Der Puy et al. |
| 6,313,360 B1 | 11/2001 | Wilson et al. |
| 6,369,285 B1 | 4/2002 | Mathieu et al. |
| 6,452,057 B1 | 9/2002 | Lambert et al. |
| 6,500,993 B1 | 12/2002 | Mathieu et al. |
| 6,500,995 B1 | 12/2002 | Branam |
| 2004/0225166 A1 | 11/2004 | Wilson et al. |
| 2005/0049443 A1 | 3/2005 | Wilson |

FOREIGN PATENT DOCUMENTS

| | | |
|---|---|---|
| EP | 0131561 | 1/1985 |
| WO | WO 97/07083 | 2/1997 |

OTHER PUBLICATIONS 2,4,6–Trimethylpyridine Article (2,4,6–Trimethylpyridine [online], [retrieved on Apr. 7, 2010] Retrieved from the Internet <URL: http://chemicalland21.com/industrialchem/organinc/2,4,6–TRIMETHYLPYRIDINE.htm>), 2 pages.

*Primary Examiner*—Dwayne C Jones

(57) ABSTRACT

A process for preparing a haloalkane comprising: (a) contacting a haloalkane starting material with an alkene in the presence of an effective amount of a catalyst complex under conditions effective to facilitate an addition reaction and to form a product stream comprising a haloalkane product from the addition reaction, wherein the catalyst complex has a boiling point higher than that of the haloalkane product; and (b) recovering the haloalkane product from the product stream.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 2, 4-7, 9, 11, 14-20 and 23 are cancelled.

Claims 3, 8, 10, 12, 13, 21, 22, 24 and 25 were not reexamined.

\* \* \* \* \*